United States Patent [19]
Van Gelder et al.

[11] Patent Number: 5,424,841
[45] Date of Patent: Jun. 13, 1995

[54] APPARATUS FOR MEASURING SPATIAL DISTRIBUTION OF FLUORESCENCE ON A SUBSTRATE

[75] Inventors: Ezra Van Gelder, Belmont; Bee C. Liang, Sunnyvale; Richard F. Johnston, Murphys; Robert T. Loder, Jr., Sunnyvale, all of Calif.

[73] Assignee: Molecular Dynamics, Sunnyvale, Calif.

[21] Appl. No.: 69,150

[22] Filed: May 28, 1993

[51] Int. Cl.6 ............................................. G01N 21/64
[52] U.S. Cl. .................................. 356/417; 250/458.1
[58] Field of Search ............... 356/417, 317, 318, 243; 250/458.1, 459.1

[56] References Cited

U.S. PATENT DOCUMENTS

| | | | |
|---|---|---|---|
| 4,811,218 | 3/1989 | Hunkapiller et al. | 364/413.01 |
| 4,833,332 | 5/1989 | Robertson, Jr. et al. | 250/458.1 |
| 4,877,966 | 10/1989 | Tomei et al. | 250/458.1 |
| 4,971,677 | 11/1990 | Kambara et al. | 204/299 R |
| 5,051,162 | 9/1991 | Kambara et al. | 204/299 R |
| 5,062,942 | 11/1991 | Kambara et al. | 204/299 R |
| 5,100,529 | 3/1992 | Fujii | 204/299 R |
| 5,243,401 | 9/1993 | Sinya | 356/243 X |

FOREIGN PATENT DOCUMENTS

0459278A1  12/1991  European Pat. Off. .

*Primary Examiner*—Vincent P. McGraw
*Attorney, Agent, or Firm*—Schneck & McHugh

[57] ABSTRACT

A fluorescence detection scanner and method employing a fiberoptic collector, positioned adjacent to the scanning plane of the excitation beam, with a light collecting surface which is oriented to reject back-scattered excitation light from the incident surface of the sample support. The scanning plane of the excitation beam is off normal relative to the incident surface of the sample support and the light collecting surface is located within the area defined by the resulting acute angle of incidence. The light collecting surface is angled away from the location at which the incident excitation beam intersects the surface of the sample support so that back-scattered excitation light does not enter the optical fibers. The orientation of the light collector results in a four to five-fold decrease in excitation-light background without attenuation of the fluorescence emitted by the sample. Long-pass interference filters, selected to reject the excitation wavelength, are located at the input and output surfaces of the fiberoptic light collector to further reduce background excitation light. Multiple fluorophores are discriminated by sequentially scanning the sample with a different interchangeable narrow bandpass filter for each fluorophore. Internal fluorescence standards in the sample are used to determine filter efficiencies for each label in each filter image and the quantity of each fluorophore is computed by linear analysis. Increased detector sensitivity allows linear quantitation of multiple fluorophores in the femto-mole range.

16 Claims, 2 Drawing Sheets

APPARATUS FOR MEASURING SPATIAL DISTRIBUTION OF FLUORESCENCE ON A SUBSTRATE

FIELD OF THE INVENTION

The invention relates generally to fluorescence detection scanners and more particularly to a scanner for gels, transfer membranes, microtiter plates and the like, wherein the optical collecting means reduces the collection of back-scattered excitation radiation.

BACKGROUND ART

Fluorescence detection is rapidly gaining acceptance as the detection method of choice in a growing number of laboratory procedures. These include for example, automated DNA sequencing and a variety of immunoassays. In response to excitation, fluorescent dyes emit light at characteristic wavelengths which differ from the excitation wavelength. Multiple labels can be discriminated in a sample by selecting dyes which have distinguishable emission wavelengths. While fluorescence detection is able to rapidly discriminate small quantities of multiple labels, fluorescence detection scanners have generally been limited to qualitative determination of the location and relative concentrations of the labels.

Fluorescent labels are generally detected by directing an excitation beam at the label and collecting the resulting fluorescent emission. The intensity of the excitation beam is much greater than the intensity of the fluorescent emission produced by the excited label. Consequently, scattered excitation light which reaches the detector results in a high light background which significantly decreases the sensitivity of the instrument and interferes with quantitation of the labels.

A variety of electrophoresis instruments with integrated fluorescence detection systems are known. U.S. Pat. Nos. 4,971,677, 5,051,162 and 5,062,942, Kambara et al., describe systems in which excitation beams are directed at the side edges of electrophoretic gels, transverse to the electrophoretic pathways. Two-dimensional fixed detectors are positioned normal to the excitation beam path and located beneath, or to the side of, the gels.

Hunkapiller U.S. Pat. No. 4,811,218, et al., describes a real time scanning electrophoresis instrument in which a fixed location in the electrophoretic pathways is repetitively scanned by a moving excitation beam and detector. One of four interchangeable bandpass filters is positioned in the detection beam path of a collector lens for each sequential scan. A Fabry lens group, which images the collector lens, is located between the bandpass filters and a photomultiplier. The excitation beam is diverted toward the gel by a Brewster angle mirror to minimize polarized light scatter that interferes with fluorescence detection. The detection beam path is normal to the gel surface at a fixed angle relative to the excitation beam. The detector and Brewster angle mirror are fixed to a stage which moves back and forth across the gel to scan individual lanes.

U.S. Pat. No. 4,833,332, Robertson, Jr. et al., describes a scanning fluorescent detection system having dual detectors with complementary wavelength-selective filters. Multiple fluorophores having closely spaced overlapping emission spectra are discriminated by the ratio of the two detector outputs. An excitation beam is swept across the electrophoresis gel in a direction transverse to the electrophoretic pathways by a rotating mirror. The detectors are located on either side of the plane in which the excitation beam travels. The excitation beam plane is normal to the gel surface and the detectors simultaneously receive inputs from all points of the scanning path. A transmission filter, which rejects light having an angle of incidence less than 69 degrees, is placed between the wavelength selective filters and the gel to eliminate scattered excitation light and emitted fluorescence which would otherwise pass through the wavelength selective filters independent of the specified filter characteristics.

Two-dimensional scanners for post-separation fluorescence detection are also known. Laid-open European patent application 0 459 278 A1, describes a fluorescence pattern reading apparatus in which a post-separation electrophoresis gel or transfer membrane is moved past an excitation beam which sweeps a scanning path transverse to the sample's direction of motion. The scanning plane of the excitation beam is normal to the sample surface and a single detector is located adjacent to the scanning plane. A lens is placed between the sample and the detector's light collector to focus back-scattered excitation light, from the surface of the gel support, to a location separate from the light collecting surface of the detector. A pair of lenses separated by a diaphragm are placed between the light collector and a photomultiplier to extract the parallel light components of the inputted fluorescence. The parallel light components are directed to an optical filter which removes the components of scattered light and then focused on the photomultiplier by a third lens.

U.S. Pat. No. 4,877,966, Tomei et al., describes an apparatus for measuring low-level laser-induced fluorescence in tissue samples in which an optical detector is placed on the opposite side of the target from the excitation beam. A bias-cut fiberoptic face plate is positioned between the target and detector to reject the excitation light, which is normal to the face plate surface.

A large portion of the interfering excitation-light background arises from light scattering at the intersection of the incident excitation beam and sample support. Prior art attempts to reduce the interfering excitation-light background have done so at the cost of attenuating the fluorescence emission signal. Systems employing lenses in the light detection path suffer from the inherent optical inefficiency of lenses. Optically efficient systems, employing fiberoptic collectors or filters, generally have light collecting surfaces which reject a portion of the fluorescence emission as well as the scattered excitation light.

It is therefore an object of the present invention to provide an improved two-dimensional fluorescence detection scanner capable of selectively reducing excitation-light background without attenuating the fluorescence emission signal.

SUMMARY OF THE INVENTION

The above object has been achieved in a fluorescent imager with a fiberoptic collector positioned and oriented to selectively reject background excitation light which scatters off the incident surface of the sample support. The term "incident location" as used hereinafter refers to the location at which the incident excitation beam intersects the surface of the sample support. The term "scanning path" refers to the locations at which the excitation beam intersects the fluorophore-containing sample. The term "incident angle" refers to the angle between the scanning plane of the excitation beam and the surface upon which the beam is incident. The incident angle of the excitation beam in the present invention is off normal and a fiberoptic light collector is positioned within the area defined by the resulting acute incident angle, and immediately adjacent to the incident location. The light collecting surface of the fiberoptic collector is angled away from the incident location so that back-scattered excitation-light from the incident location does not enter the optical fibers, whose optical axis is directed at the scanning path.

In the preferred embodiments, the sample support is an optically transparent stage which moves the sample in the direction transverse to the linear scanning path. The fiberoptic light collector is located beneath the stage, adjacent to the surface upon which the excitation beam is incident. The fiberoptic light collector has a long-pass filter, selected to reject the wavelengths contained in the excitation beam, located on its light collecting surface. A second long-pass filter is located on the output surface of the fiberoptic collector for reducing any remaining background excitation light. The collected fluorescent emission is then directed at a filter changer which positions one of a number of narrow bandpass filters, corresponding to the peak emission wavelength of the fluorophores, between the light collector and a photomultiplier.

The sample is sequentially scanned at each selected wavelength to produce an image intensity map corresponding to each filter. The location-specific image intensity signals from the photomultiplier are stored in a computer. Fluorophore standards contained in the sample are used to determine the constant filter efficiencies of each filter for each label. The amount of each fluorophore at a particular location can be quantitatively determined from the filtered image intensities for that location and the constant filter efficiencies using conventional linear analysis, as described herein below.

An advantage of the fluorescent detection scanner of the present invention is that the light collector selectively reduces background excitation-light without attenuating the fluorescent emission signal from the sample.

BEST MODE FOR CARRYING OUT THE INVENTION

Figure 1:
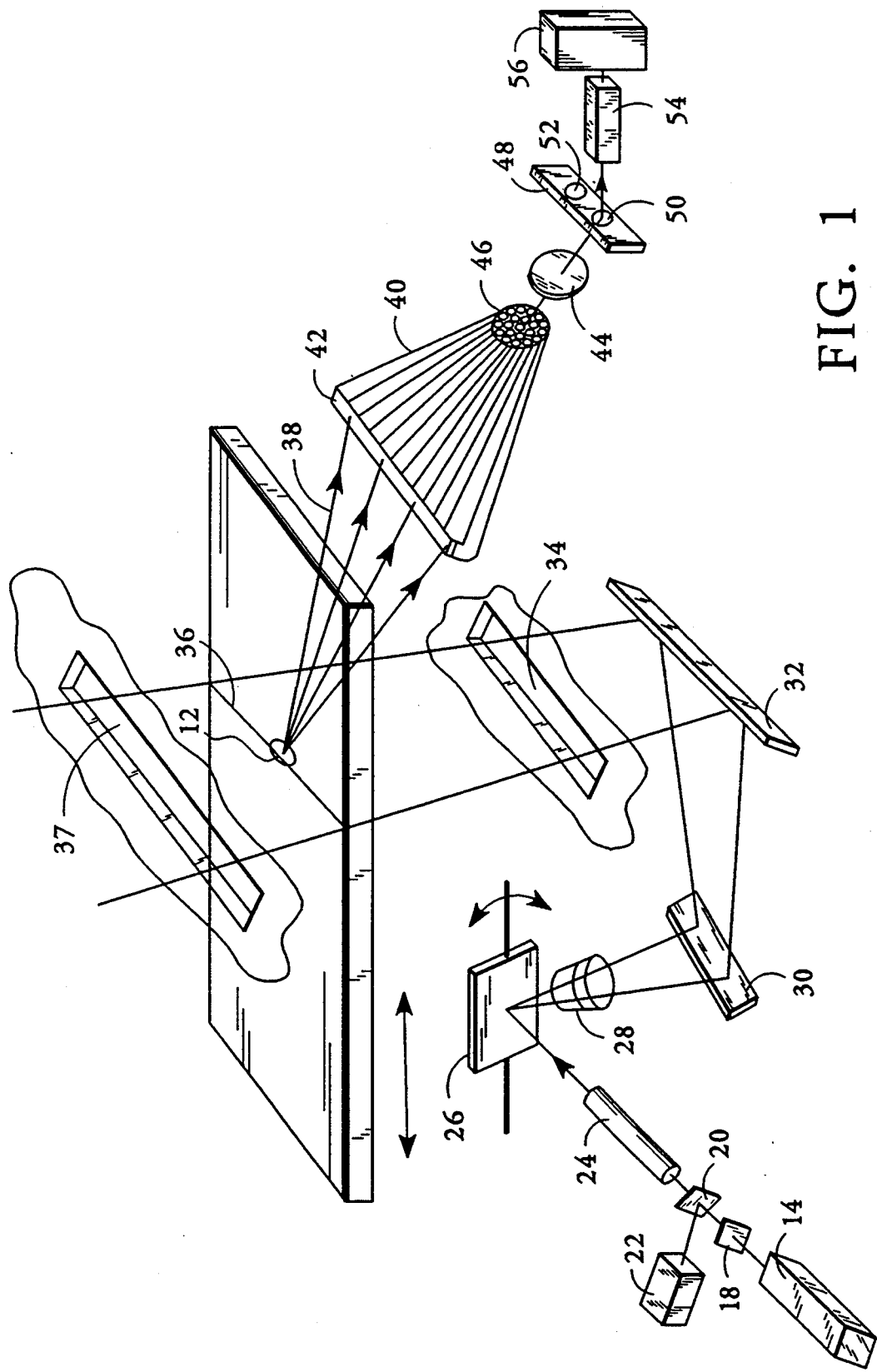
FIG. 1 is a perspective plan view of a two-dimensional fluorescence detection scanner in accordance with the present invention.

Referring to FIG. 1, a perspective plan view of a fluorescence detection scanner embodying the present invention is shown. A sample translation stage 10 supports a fluorophore-containing sample 12 and moves, relative to the optics shown immediately below, in the direction indicated by the arrows. The scanning beam is generated by a laser in the following manner. A laser 14 generates a beam 16 toward a filter 18 which passes the selected excitation wavelengths. The filtered beam passes through a beamsplitter 20 which directs a portion of the beam to a reference detector 22 used to monitor the beam intensity. The remainder of the beam is directed to a beam expander 24 which controls the size of the scanning spot. The excitation-beam spot size will vary with the desired pixel dimensions and in the preferred embodiment is <200 microns in diameter and most preferably 5–50 microns in diameter. The expanded beam is directed toward a galvanometer mirror 26 which controls the location of the excitation beam within the scanning path. Galvanometer mirror 26 includes a spindle support and rotates about a pivot axis perpendicular to the optical axis as indicated by the arrows. An optical f-theta correcting lens 28 is provided in the reflected beam path to correct for tangential spacing errors in the image plane. A pair of laser-quality plane mirrors 30 and 32 direct the scanning beam through a slit 34 in a light-tight enclosure, not shown, toward sample stage 10 where it is incident along a line 36. The excitation beam exits the light-tight enclosure through a second slit 37 leading to a fibrous light trap, not shown. Preferably, laser 14 is a 4 to 40 mW argon laser emitting a 488 nm excitation wavelength. Other lasers, such as for example, a HeNe laser emitting at 633 nm or laser diode, may also be employed with the excitation wavelengths being selected to excite the fluorophores to be detected.

Fluorescent light emitted by the sample in response to the excitation beam is indicated by a scattering pattern 38. Light emitted by the excited fluorophores is collected by a fiberoptic bundle 40 after passing through a long-pass filter 42 which selectively passes wavelengths longer than the wavelengths contained in the excitation beam. A second long-pass filter 44 having similar wavelength transmission characteristics is located between the output surface 46 of fiberoptic bundle 40 and a filter changer 48 containing a pair of interchangeable narrow-bandpass filters 50 and 52 selected to pass wavelengths corresponding to the peak emission wavelengths of the selected fluorophores. The wavelength transmission characteristics of bandpass filters 50 and 52 will vary depending upon the particular fluorescent dyes selected. The nominal center wavelength of each filter will be chosen to correspond to the peak emission wavelength of one of the dyes. Filters with a bandpass of 10 nm (as measured at the 50% transmission point) are commercially available, for example, from Melles Griot, Irvine, Calif.

The filtered beam is directed toward a photomultiplier 54 which produces a signal corresponding to the intensity of the filtered light. Photomultiplier 54 is connected to a computer 56 which stores the signal intensities in a location-specific manner corresponding to the position of the scanning beam. Computer 56 also receives input from filter changer 48, galvanometer mirror 26 and translation stage 10 to identify the location of the excitation beam on the sample.

In operation, the excitation beam is continuously scanned back and forth across line 36 and the entire sample is imaged by moving sample stage 10 in the direction perpendicular to the beam path. Fiberoptic bundle 40 simultaneously receives input from the entire scanning path. Computer 56 samples the intensity signal output by photomultiplier 54 with a pixel size range of 25 microns to 200 microns. The pixel location is determined by correlating the inputs from galvanometer mirror 26 and sample translation stage 10. The maximum sample size is determined by the nature of the sample and in one preferred embodiment is 20×25×1.2 cm with the read time being less than 3 minutes for a complete one-color scan at a 100 micron pixel size. Following a complete scan of the sample with bandpass filter 50, filter changer 48 replaces filter 50 in the beam path with filter 52 and the sample is completely scanned a second time with filter 52.

Figure 2:
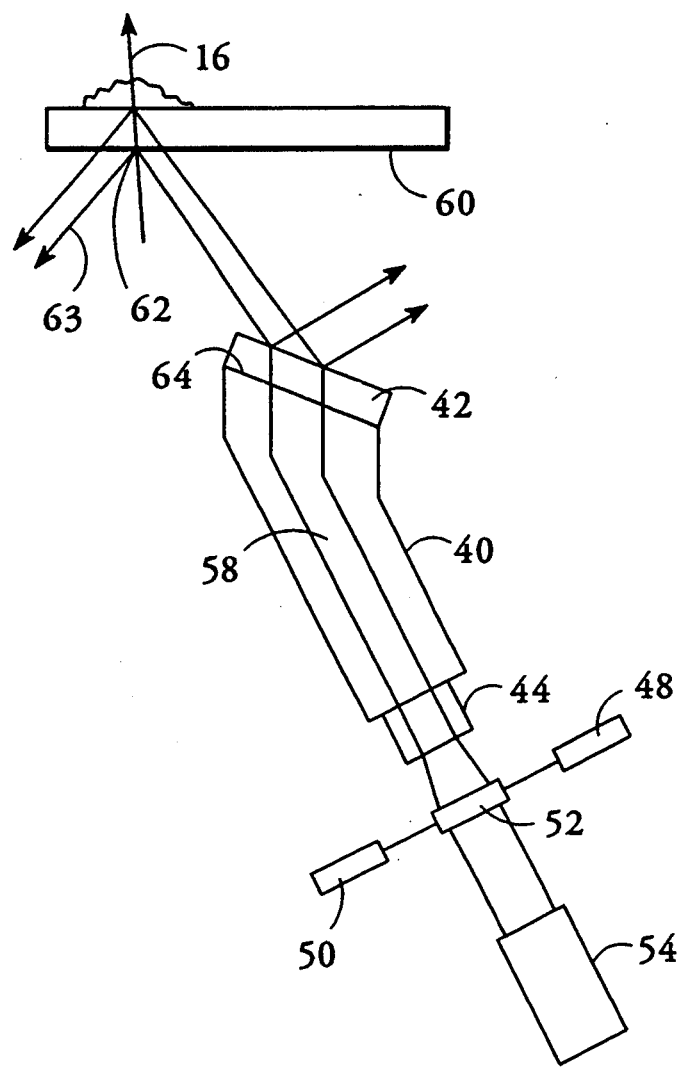
FIG. 2 is a schematic view of the detection optics.

Referring now to FIG. 2, the detection optics are shown in greater detail. Excitation beam 16 is incident upon a lower surface 60 of sample stage 10 at an incident location 62. The angle of incidence of beam 16 is off normal relative to surface 60 and fiberoptic bundle 40 is located within the area defined by the acute angle of incidence in order to minimize collection of reflected excitation light 63. In the preferred embodiments the incident angle of excitation beam 16 relative to surface 60 is between ninety degrees and eighty degrees. Fiberoptic bundle 40 contains a plurality of optical fibers 58 with input ends arranged in a rectangular array to form a light collecting surface 64.

Figure 3:
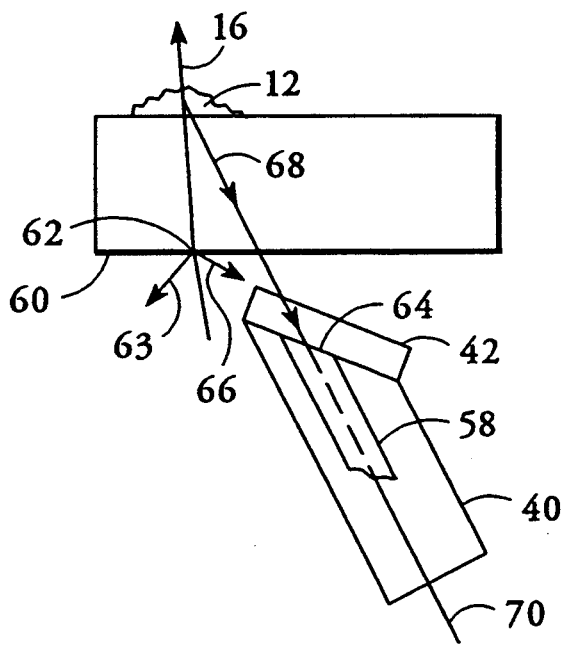
FIG. 3 is an exemplary view showing the orientation of the light collecting surface relative to the excitation beam path and the sample support surface.

Referring now to FIG. 3, the orientation of light collecting surface 64 relative to incident location 62 of excitation beam 16 is shown in greater detail. By angling light collecting surface 64 away from incident surface 60, back-scattered excitation light 66 originating at incident location 62 falls on light collecting surface 64 at an angle outside the acceptance angle of fibers 58. The fluorescent emission 68 however, originating at the scanning-path location in sample 12, enters light collecting surface 64 on the optical axis 70 of optical fibers 58 and is transmitted along the fibers by internal reflection. The position and orientation of light collecting surface 64 relative to excitation beam 16 and incident surface 60 results in the selective rejection of back-scattered excitation light 66 by optical fibers 58 without attenuation of fluorescent emission 68 from sample 12.

The angle of inclination necessary to reject back-scattered excitation light 66 will vary depending upon the relative positions of light collecting surface 64 and incident location 62. The incident angle of back-scattered excitation light 66 on light collecting surface is preferably less than 5 degrees. At such angles, back-scattered excitation light is reflected by light collecting surface 64 and does not enter fibers 58. In the preferred embodiment, light collecting surface 64 is located immediately adjacent to incident location 62 within 1 mm of incident surface 60 and at least 200 microns distant from excitation beam 16. The surface to surface separation may vary depending upon the numerical aperture of fibers 58. Eliminating back-scattered excitation light 66 from surface 60 leads to a four to five-fold decrease in the excitation-light background. The remainder of the excitation-light background is further reduced by filters 42 and 44. In the preferred embodiment, filters 42 and 44 are long-pass interference or holographic filters which selectively pass wavelengths at least 25 nm greater than the excitation wavelength used. Suitable filters are commercially available from Melles Griot, Irvine, Calif.

In the preferred embodiment, light collecting surface 64 extends across the full twenty-centimeter width of sample translation stage 10. One data pixel is gathered within a time period of 10 microseconds to 150 microseconds in the following manner. Analog electronics in photomultiplier 54 implement a signal integration function and an analog-to-digital converter samples the integrator at the end of the integration period. Each integrated data pixel adjustably spans 100 or 200 microns in the preferred embodiments.

Quantitation of two fluorophores having overlapping emission spectra (e.g. thiazole orange and bis (methyl phenoxyzone) diamine (POPO)) in the same sample is performed as follows:

The sample (gel, blot, microtiter plate, etc.) is scanned three times. First with a long pass filter with a cutoff wavelength at 515 nm. Then second with a $533 \pm 14$ nm band pass filter. A final scan is made with a $568 \pm 14$ nm band pass filter. A standard for each label is scanned along with the sample. The standards are analyzed to calculate constant efficiencies (E) for each label under both filter scans:

$$E = \frac{\text{instrument counts/mm}^2 \text{ with band pass filter}}{\text{instrument counts/mm}^2 \text{ with long pass filter}} \quad \text{(eq. 1)}$$

The three scans of the standards yield four efficiencies:

$E_{2T}$=efficiency for thiazole orange in filter 2
$E_{3T}$=efficiency for thiazole orange in filter 3
$E_{2P}$=efficiency for POPO in filter 2
$E_{3P}$=efficiency for POPO in filter 3

The two band pass filter images of the samples are then analyzed to determine the integrated fluorescent counts (C) for all spots of interest. For each spot, the values for the two images are:

$C_1$=counts/spot, filter 2

$C_2$=counts/spot, filter 3

We wish to determine the total concentration of each label in each spot. If we define $D_T$ and $D_P$ as a total fluorescent emission per spot from thiazole orange and POPO respectively, then:

$$C_1 = E_{2T}D_T + E_{2P}D_P \quad \text{(eq. 2)}$$

$$C_2 = E_{3T}D_T + E_{3P}D_P \quad \text{(eq. 3)}$$

Solving these simultaneous equations for $D_T$ and $D_P$ we obtain:

$$D_T = \frac{E_{2P}C_2 - E_{3P}C_1}{E_{2P}E_{3T} - E_{2T}E_{3P}} \quad \text{(eq. 4)}$$

$$D_P = \frac{E_{3T}C_1 - E_{2T}C_2}{E_{2P}E_{3T} - E_{2T}E_{3P}} \quad \text{(eq. 5)}$$

The amounts of the two labels are determined using equations 4 and 5.

Although the equations shown here refer to thiazole orange and POPO, the method applies to any two labels whose fluorescent emission wavelengths differ enough that they can be adequately resolved by suitable filters. Other representative dyes include bodipy, fluorescein and the like.

The fluorescence detection system of the present invention produces a 1 to 2 orders of magnitude increase in detection sensitivity which allows linear quantitation of fluorescent dyes in the femto-mole range. The increased linear detection sensitivity of the present invention allows dyes having overlapping emissions spectra to be quantitatively discriminated using the linear analysis technique described above.

We claim:

1. Apparatus for measuring the spatial distribution of fluorescence on a substrate having multiple fluorophores each having a different characteristic wavelength comprising:

scanning means for directing a radiant excitation beam at known locations on a substrate containing a plurality of fluorophore targets, said locations defining a scanning path;

collecting means for simultaneously collecting radiation from the scanning path;

detecting means positioned to receive radiation from said collecting means, said detecting means producing a signal corresponding to the intensity of said collected radiation;

first filter means positioned between said collecting means and said scanning path, said first filter means selectively rejecting background wavelengths contained in said excitation beam;

second filter means positioned in the radiation path between said collecting means and said detecting means, said second filter means selectively rejecting background wavelengths contained in said excitation beam; and third filter means for interchangeably positioning one of a plurality of band pass filters between said second filter means and said detecting means, each of said band pass filters selectively transmitting a different band of wavelengths, each of said bands being associated with a different fluorophore, whereby the distribution of fluorescence on the substrate at selected wavelengths at said known locations can be measured.

2. The apparatus of claim 1 wherein said substrate includes a planar surface upon which said excitation beam is incident and said collecting means includes a collecting surface closely spaced apart from said substrate surface for receiving radiation, said collecting surface having the property of rejecting radiation having an incident angle less than a predetermined value, said collecting surface further being oriented to reject radiation from the locations defined by the intersection of said excitation beam with said substrate surface.

3. The apparatus of claim 2 wherein the angle of incidence of said excitation beam relative to said substrate surface is less than 90° and said collecting surface is disposed adjacent to said beam intersection locations in the area bounded by said angle.

4. The apparatus of claim 2 wherein light from said intersection locations is reflected by said light collecting surface.

5. The apparatus of claim 2 wherein said collecting surface rejects radiation having an angle of incidence less than five degrees.

6. The apparatus of claim 2 wherein the separation between said collecting surface and said substrate surface decreases in the direction toward said beam intersection locations.

7. The apparatus of claim 2 wherein said collecting means includes a bundle of elongated optical fibers, each of said fibers having an input end located on said collecting surface.

8. The apparatus of claim 7 wherein the optical axis of each of said fibers is directed toward said scanning path.

9. The apparatus of claim 2 wherein said first filter means is coextensive with, and substantially parallel to, said collecting surface.

10. The apparatus of claim 9 wherein said filter means is in area-wise contact with said collecting surface.

11. The apparatus of claim 10 wherein said filter means includes a long-pass filter which selectively transmits wavelengths longer than the wavelengths contained in said excitation beam.

12. The apparatus of claim 11 wherein said filter is an interference filter or a holographic filter.

13. The apparatus of claim 2 wherein said detecting means is located at a remote location relative to said collecting surfaces.

14. The apparatus of claim 1 characterized by the absence of a lens between said detecting means and said substrate.

15. The apparatus of claim 1 wherein said scanning means includes stage means for translating said substrate in a direction transverse to said scanning path.

16. The apparatus of claim 1 further including:

computer means coupled to said scanning means and said third filter means for controlling said third filter means and said scanning means, for receiving intensity signals from said detecting means, and for correlating said intensity signals with the corresponding known locations of said excitation beam on said substrate and the corresponding transmission filter in said third filter means; and memory means coupled to said computer means for storing said correlated signal intensities in a location-specific manner, whereby a signal intensity map of said substrate for each of said transmission filters can be produced.

* * * * *